United States Patent [19]
Burns

[11] Patent Number: 5,527,513
[45] Date of Patent: Jun. 18, 1996

[54] COLLECTION ASSEMBLY

[75] Inventor: James A. Burns, Elizabeth, N.J.

[73] Assignee: Becton Dickinson and Company, Franklin Lakes, N.J.

[21] Appl. No.: 225,029

[22] Filed: Apr. 8, 1994

[51] Int. Cl.⁶ .............................. B65D 41/18; C12M 1/24
[52] U.S. Cl. ...................... 422/102; 128/763; 128/767; 215/295; 215/318; 215/321; 215/354; 220/306; 422/99; 435/307.1; 494/16
[58] Field of Search ........................ 128/763, 764, 128/765, 766, 767; 215/295, 318, 321, 354; 220/260, 306; 422/99, 102; 435/296; 494/16

[56] References Cited

U.S. PATENT DOCUMENTS

| | | | |
|---|---|---|---|
| 2,039,037 | 4/1936 | Simpson | 220/301 |
| 2,193,226 | 3/1940 | Deletzke | 215/295 |
| 2,867,351 | 1/1959 | MacLeod | 220/260 |
| 3,136,458 | 6/1964 | Ruetz | 222/498 X |
| 3,308,039 | 3/1967 | Nelson | 435/296 X |
| 3,372,834 | 3/1968 | Ayotte et al. | 220/306 |
| 3,419,179 | 12/1968 | Deuschle et al. | 220/306 |
| 3,430,798 | 3/1969 | Goyet et al. | 215/295 |
| 3,784,047 | 1/1974 | Cooper | 220/40 R |
| 3,901,400 | 8/1975 | Westfall | 215/221 |
| 3,902,477 | 9/1975 | Gerade | 128/2 F |
| 3,910,444 | 10/1975 | Foster | 215/295 |
| 3,913,783 | 10/1975 | Cooper | 220/300 |
| 3,945,525 | 3/1976 | Jones | 215/232 |
| 3,982,651 | 9/1976 | Braun et al. | 220/4 B |
| 4,117,946 | 10/1978 | Kessler | 215/321 |
| 4,171,057 | 10/1979 | Gach | 215/211 |
| 4,204,605 | 5/1980 | Ravn et al. | 215/295 |
| 4,335,823 | 6/1982 | Montgomery et al. | 215/206 |
| 4,390,111 | 6/1983 | Robbins et al. | 220/259 |
| 4,576,185 | 3/1986 | Proud et al. | 128/760 |
| 4,577,769 | 3/1986 | Delia | 215/211 |
| 4,805,635 | 2/1989 | Korf et al. | 128/763 |
| 4,858,777 | 8/1989 | Morel | 215/295 |
| 5,288,466 | 2/1994 | Burns | 422/102 |
| 5,320,233 | 6/1994 | Welch | 215/252 |

FOREIGN PATENT DOCUMENTS 2041892  9/1980  United Kingdom.

Primary Examiner—Jill Warden
Assistant Examiner—Harold Y. Pyon
Attorney, Agent, or Firm—Alan W. Fiedler

[57] ABSTRACT

The present invention is a collection assembly useful for collecting small quantities of blood. The assembly comprises a container with an integral lip for facilitating collection of the blood and a cap suitable for enclosing the container. The assembly further comprises a sealing arrangement for securing the cap with the container and a cam follower within the cap that interacts with the integral lip of the container to unsecure the cap from the container.

10 Claims, 6 Drawing Sheets

COLLECTION ASSEMBLY

BACKGROUND OF THE INVENTION

1. Field of the Invention

The present invention relates to a collection assembly and, more particularly, to a microcollection container and cap suitable for collecting small quantities of blood from a patient and maintaining the blood in secure fashion for subsequent testing.

2. Description of Related Art

Analytical instrumentation has made it possible to carry out a variety of hematological diagnostic procedures on very small quantities of blood. Because of this, a patient's finger or earlobe, for example, may be punctured and a very small quantity of blood may be rapidly collected into a container for such testing. However, in order to carry out testing and analysis on small quantities of blood, the blood must be rapidly collected prior to any coagulation thereof.

A collection arrangement as described in U.S. Pat. No. 5,288,466, has been provided wherein a cap having a sealing element is configured to fit the top of a microcollection container having a lip for engaging the puncture site and transferring blood to the container. However, with such an arrangement, when a sample is taken, blood droplets may be left in and around the top area of the container or on the bottom of the sealing element. Therefore, excess blood may be aspirated when the cap is removed from the top of the container.

SUMMARY OF THE INVENTION

The present invention is a collection assembly comprising a container and a cap. The cap preferably comprises a closed top portion, an open bottom portion, and an annular skirt extending from the top portion to the bottom portion having an inner surface and an outer surface. The cap further includes an inner inverted skirt portion having a sealing ring at its extremity that is surrounded by the inner surface of the annular skirt. Most preferably the inner inverted skirt portion is separated from the inner surface of the annular skirt by an annular space, with the cap including a cam follower positioned on the top portion. Desirably, the inside surface of the annular skirt comprises at least one protrusion and the inner inverted skirt portion has a sealing ring. The cap further comprises a shield extending from the outer surface of the annular skirt at its open end.

The container preferably comprises an open top portion, a closed bottom portion, a sidewall extending from the top portion to the bottom portion and an open end associated with the top portion having an integral collector or lip portion. Most preferably the integral collector is a scoop that is the same diameter as the inner diameter of the container so that no air vent is required.

Preferably, the container further includes a cap seating flange associated with the outer diameter of the top portion of the container and an extending annular skirt associated with the bottom portion. Most preferably, a blood trap or trough is positioned within the cap seating flange and a locking ring is associated between the integral collector and the cap seating flange.

Preferably, the collection assembly includes means for securing the inner surfaces of the cap to the top portion of the container by the interaction of the protrusions of the cap with the locking ring of the container and the sealing ring of the cap with the inside surface of the top portion of the container. Most preferably, the collection assembly also includes means for unsecuring the cap from the container by a cam arrangement on the cap and container. This cam arrangement assists in substantially reducing fluid splatter from the container when the cap is removed from the container.

In a preferred embodiment of the invention, the cam arrangement includes at least one cam follower positioned on the top portion of the cap and a pair of cam surfaces on the integral lip of the container. A downward rotational force applied to the cap and an upward force applied to the container along the longitudinal axis, causes the cam follower and a cam surface to align and the cap to snap-seal to the container by the interaction of the protrusions of the cap with the locking ring of the container and the sealing ring of the cap with the inside surface of the top portion of the container. This action, which may cause an audible-snap, in turn seals the container by compressing the protrusions of the cap against the locking ring of the container and the sealing ring of the cap against the inside surface of the top portion of the container to form a non-permanent lock and to substantially prevent the outer surface of the top portion of the container from making contact with the inside surface of the cap's annular skirt.

The cap and container are then unsecured in a twist off manner by applying a rotational force to the cap. Most preferably, an upward rotational force is applied to the cap and a downward force is applied to the container along the longitudinal axis. This causes the cam follower to rise on one of the cam surfaces and in turn the cap is unsecured from the container. An important advantage of the present invention is that the rotational force applied to the cap can be bi-directional, that is clockwise or counter-clockwise.

An advantage of the present invention is that any excess fluid on the outside surface of the integral collector is directed downward into the blood trap or trough of the cap seating flange when a downward force is applied to the cap as the cap and container are being secured. Therefore, radial spray of excess fluid is minimized.

Still another advantage of the invention is that the recessed inverted skirt and the sealing-ring substantially reduce cap contact with fluid collected in the container. Therefore the inner surfaces of the cap may be minimally exposed to fluid collected in the container when the cap is secured to the top portion of the container and again radial spray of excess fluid is minimized during cap removal.

Another advantage of the present invention is that the outer surface of the cap may preferably be configured to substantially limit movement or rolling of the cap or the assembly. This applies whether the cap is positioned within the top portion or bottom portion of the container.

Another advantage of the present invention is that when the cap is secured to the container, the rim of the cap substantially prevents contamination to the specimen inside the container. In addition, when the cap is secured to the container the flange on the container is not covered completely by the shield on the cap, so that when the capped assembly is centrifuged the load is on the flange and the cap is not loosened.

DETAILED DESCRIPTION

Figure 1:
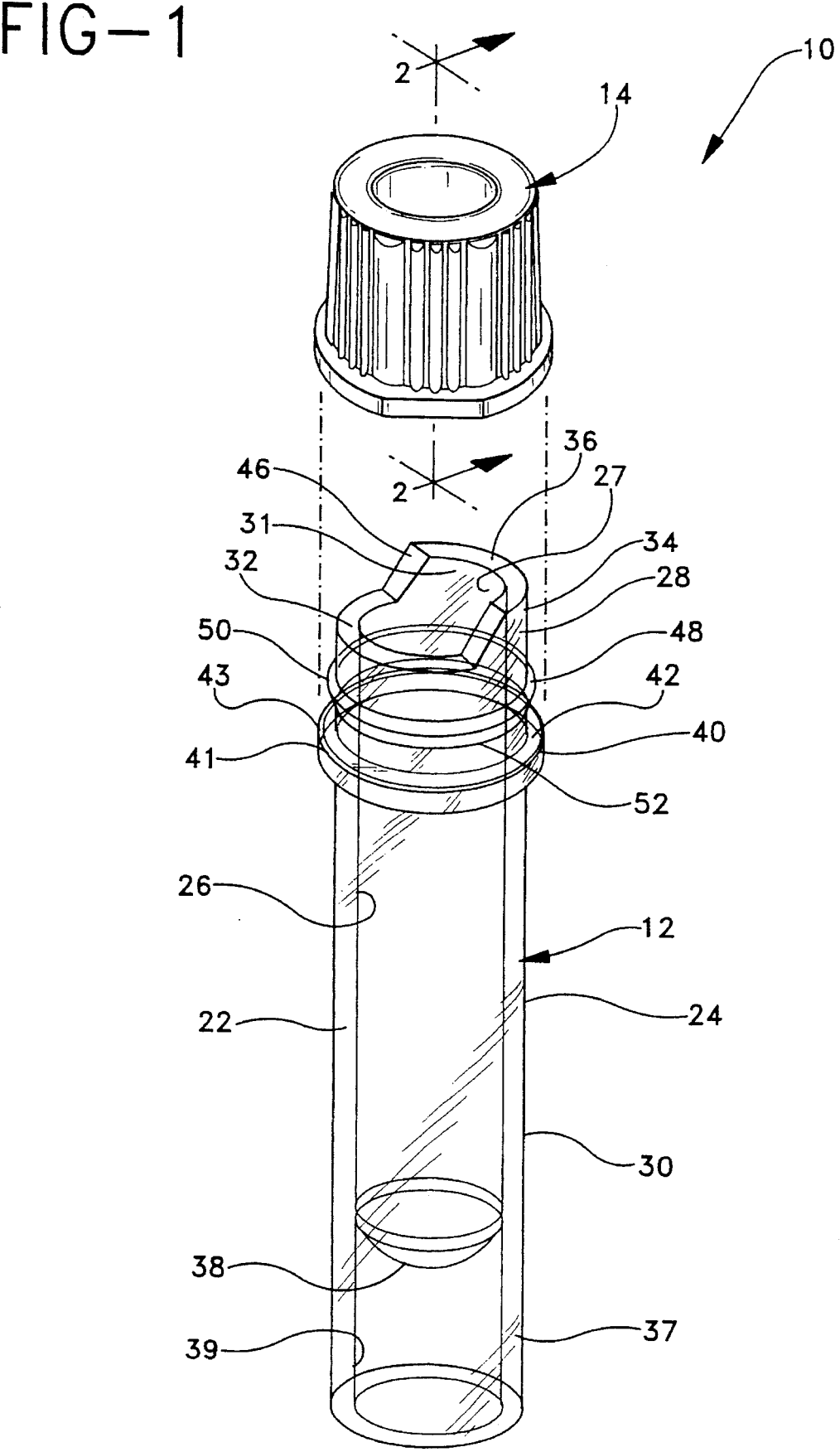
FIG. 1 is a perspective view of the preferred collection assembly illustrating the container with the cap unsecured.

Referring to the drawings in which like reference characters refer to like parts throughout the several views thereof, FIG. 1 illustrates a collection assembly 10 comprising a container 12 and a cap 14.

As illustrated in FIG. 1, container 12 has a sidewall 22 having an outer surface 24 and an inner surface 26. Sidewall 22 extends from an upper portion 28 to a lower portion 30. Upper portion 28 includes an open end 31 and an inner surface 27 with a top surface 32 having an integral lip portion 34 with a receiving edge 36 and a pair of cam surfaces 46. Lower portion 30 comprises a closed bottom end 38 and an annular skirt 37 extending from closed bottom end 38 to define a compartment area 39. Annular skirt 37 provides a means for allowing the container to be placed upright on a flat surface and means for receiving cap 14.

Upper portion 28 has a cap seating flange 40 positioned around outer surface 24 of container 12 which defines a well or trough 42 having an outer wall 41 with an upper surface edge 43. Further positioned on upper portion 28 of container 12 is a locking ring 48 that is positioned between receiving edge 36 of integral lip portion 34 and cap seating flange 40. Locking ring 48 has an upper edge 50 and a lower edge 52.

Figure 2:
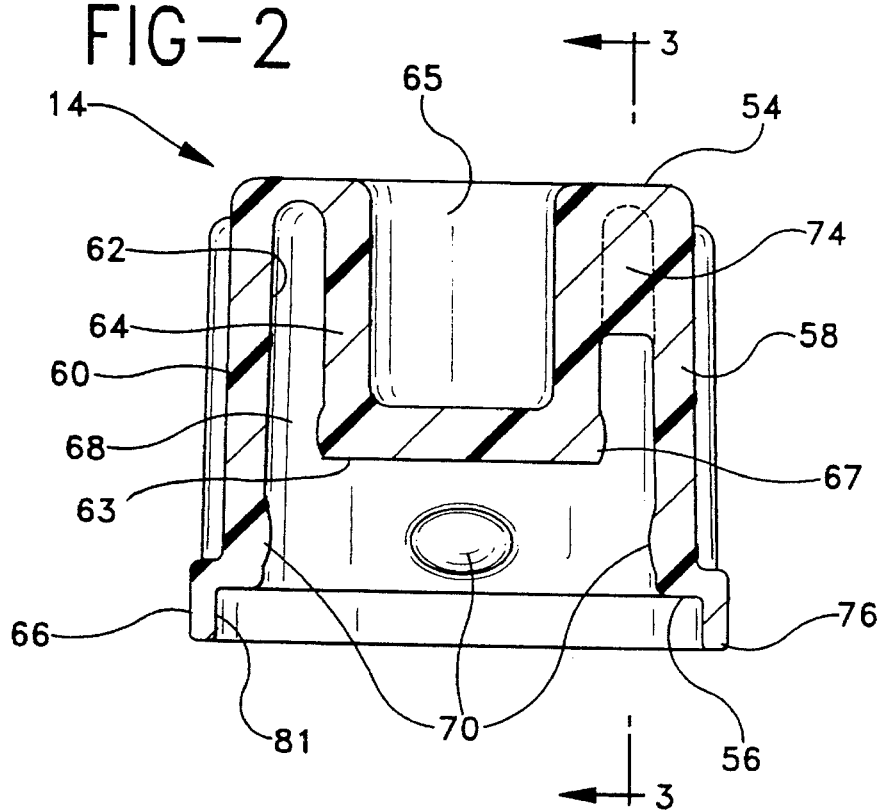
FIG. 2 is an enlarged cross-sectional view of the cap of FIG. 1, taken along line 2—2 thereof.

Cap 14 as shown in FIG. 2, has a top surface 54, a bottom stop ledge 56 and an annular outer skirt 58 extending from top surface 54 to bottom stop ledge 56. Annular outer skirt 58 has an outer wall surface 60 and an inner wall surface 62, and a shield 66 extends from the bottom of outer wall surface 60 of annular outer skirt 58 and has an outer surface or circumference 76.

Figure 3:
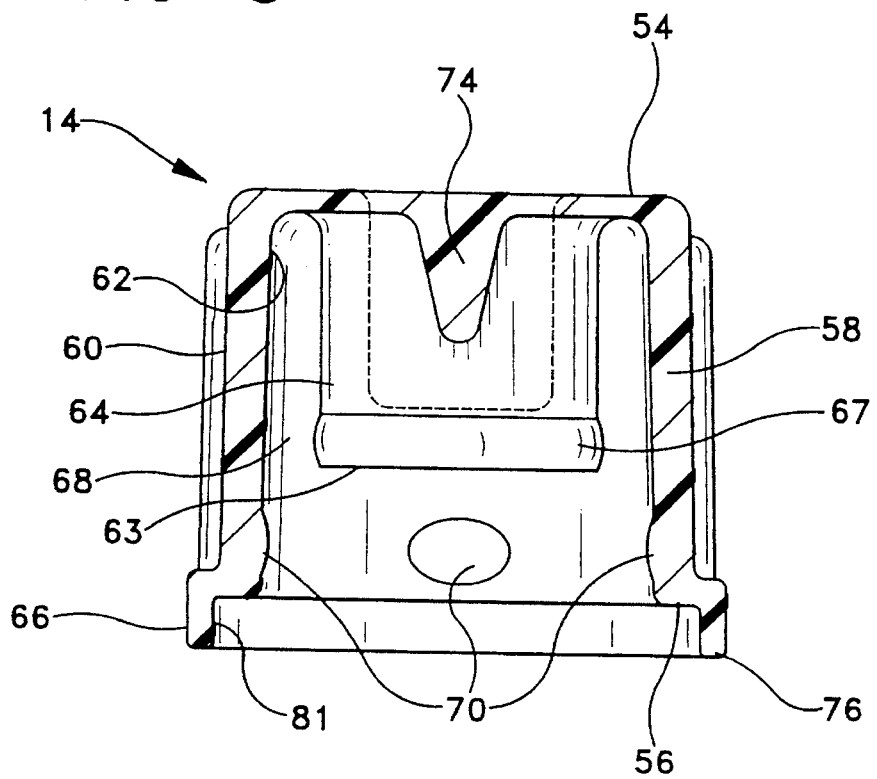
FIG. 3 is another enlarged cross-sectional view of the cap of FIGS. 1 and 2, taken along line 3—3 in FIG. 2.

As shown in FIG. 2, cap 14 also has an inner annular inverted recessed skirt 64 that extends from top portion 54 to a bottom surface 63. Inverted recessed skirt 64 defines a compartment or cup area 65 in top portion 54 of cap 14. Inner wall surface 62 of annular outer skirt 58 and inner annular inverted recessed skirt 64 are spaced from each other to define an annular space 68. The cap further includes, a plurality of circumferentially spaced protrusions 70 positioned on inner wall surface 62 and a sealing ring 67 positioned on inverted recessed skirt 64. A cam follower surface 74 extends from top portion 54 of cap 14 into annular space 68, as shown in FIGS. 2 and 3.

Figure 4:
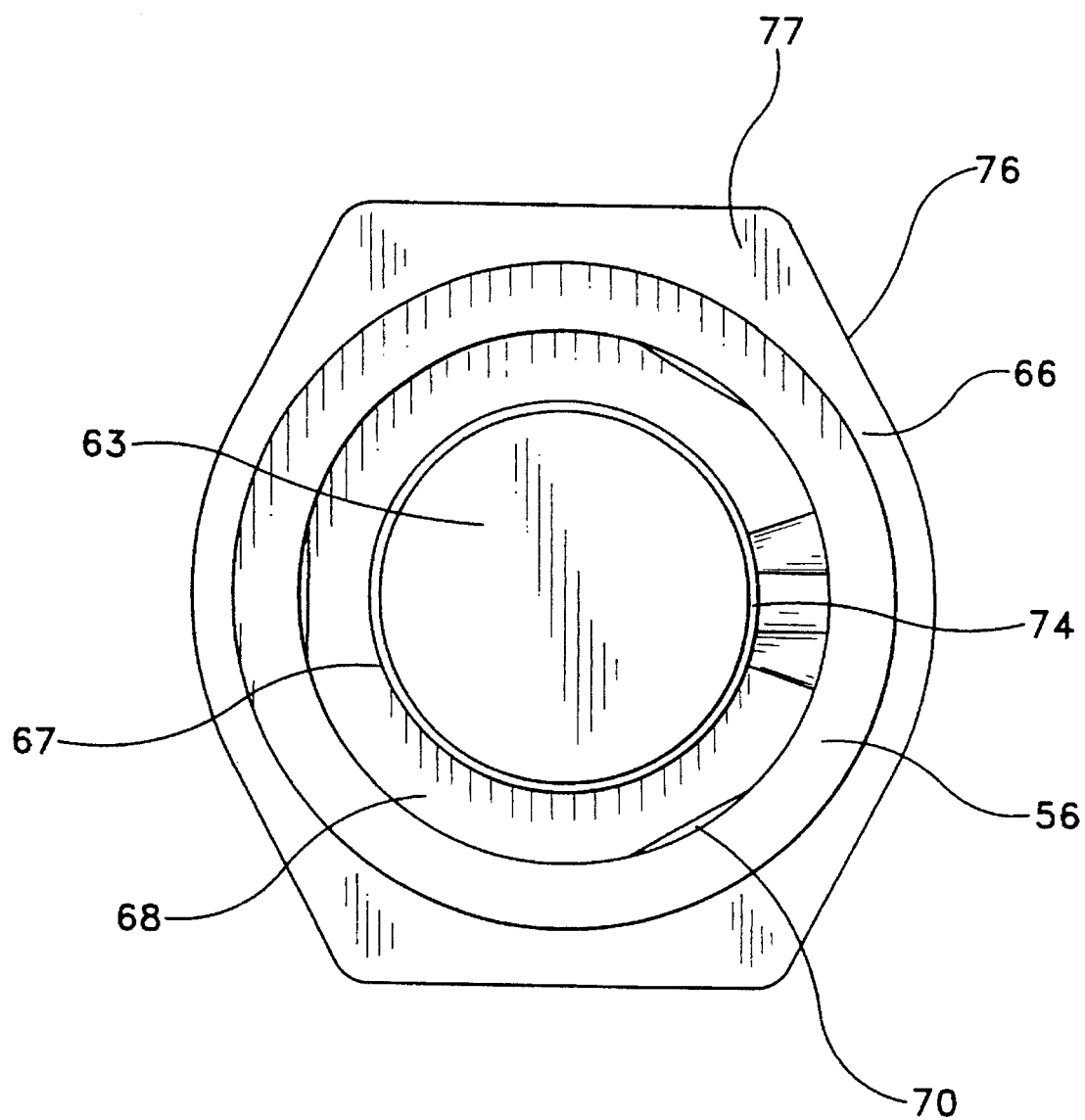
FIG. 4 is a bottom view of the cap of FIG. 1.

As shown in FIG. 4, flats 77 are positioned on outer surface 76 of shield 66. Flats 77 substantially prevent cap 14 from rolling and provide a convenient grasping surface for ready removal and placement of cap 14 on container 12. Although a shield with a smooth outer circumference without flats is within the purview of the instant invention, a shield with an outer surface with flats is preferred.

Figure 5:
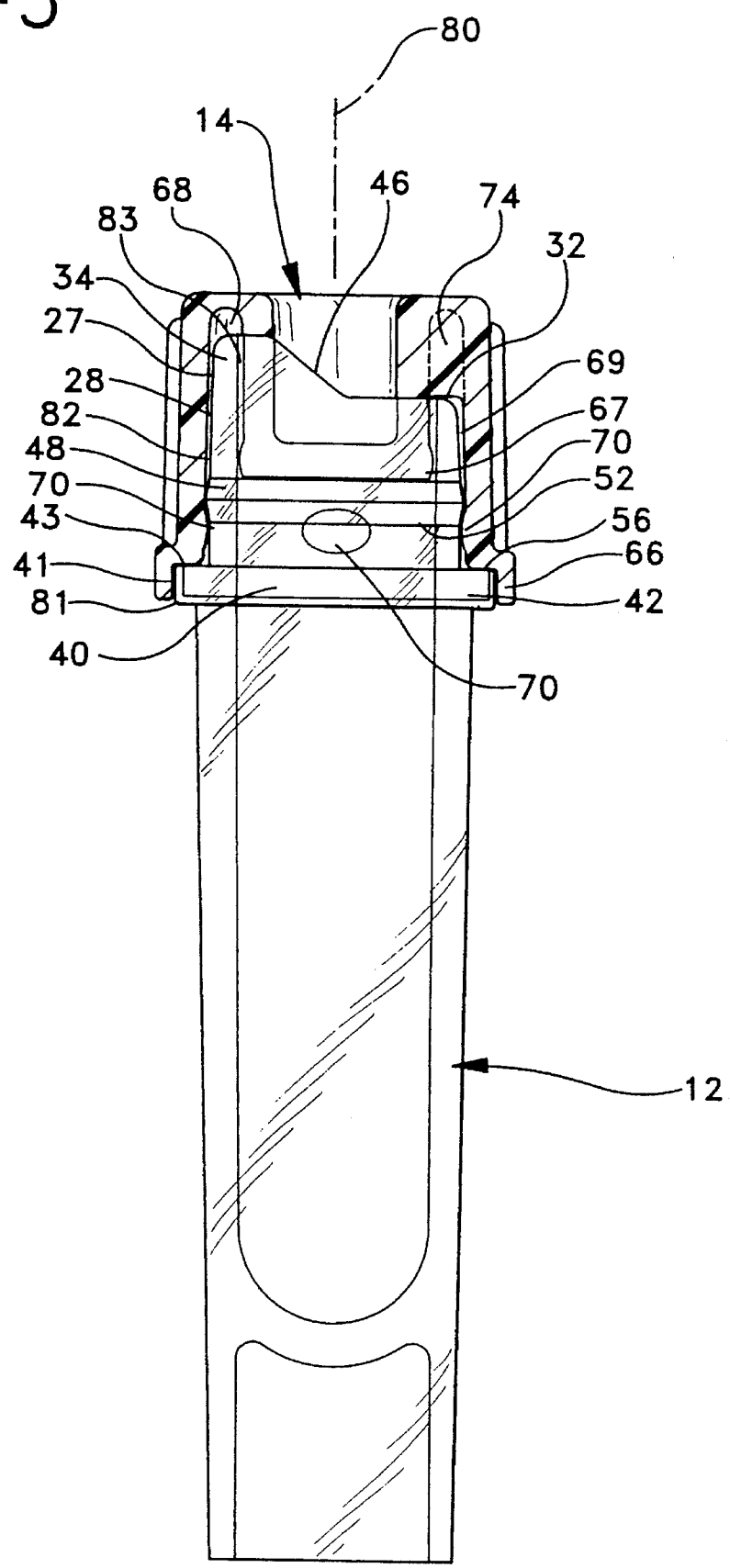
FIG. 5 is a side elevational view of the container of FIG. 1 with the cap secured thereto.

As shown in FIG. 5, when cap 14 is removably secured to container 12, space 68 of cap 14 receives upper portion 28 of container 12 including integral lip portion 34, protrusions 70 bear against lower edge 52 of locking ring 48 of container 12, sealing ring 67 bears against inner surface 27 of container 12 and cam follower 74 contacts top surface 32 on open end 31. Shield 66 covers outer wall 41 of cap seating flange 40 and bottom stop ledge 56 abuts with upper surface edge 43 of cap seating flange 40, so as to form a non-permanent lock and substantially prevent any excess fluid in well 42 of cap seating flange 40 from spilling out. Any fluid that migrates between upper surface edge 43 and bottom stop ledge 56 is directed in a downward direction along the container by an inner surface 81 of shield 66. In addition, spaces 82 and 83 remain between integral lip portion 34 and each skirt 58 and 64 to prevent blood on lip portion 34 being pushed down towards bottom stop ledge 56. Further, any fluid in well 42 is substantially contained by upper surface edge 43 of cap seating flange 40, bottom stop ledge 56 of cap 14 and inner surface 81 of shield 66. Outer surface 76 of shield 66 does not cover cap seating flange 40 of container 12 completely, as shown in FIG. 5, so that when the capped assembly is centrifuged the load is on flange 40 and cap 14 is not loosened.

Cam follower surface 74 and upper portion 28 are configured so that a downward rotational force applied to cap 14 about longitudinal axis 80 causes cam follower 74 to contact top surface 32. Preferably, cam follower surface 74 has a triangular shape, however, any shape that can easily follow top surface 32 and cause cap 14 to separate from container 12 is acceptable. Cap 14 is snapped onto upper portion 28 of container 12 as guided by cam follower surface 74 and top surface 32. Cap 14 is removably secured to container 12 by protrusions 70 and sealing ring 67 as they bear respectfully against lower edge 52 of locking ring 48 and inner surface 27 of container 12. The position of protrusions 70 and sealing ring 67 of cap 14 with container 12 forms space 69 between outer surface 24 of upper portion 28 and inner wall surface 62 of annular outer skirt 58. Therefore, wiping down of any fluid on the container's outer surface is substantially prevented. In addition, bottom stop edge 56 bears against flange upper surface 43 to provide a stop and insure proper sealing depth for sealing ring 67 on container upper inner surface 27.

Figure 6:
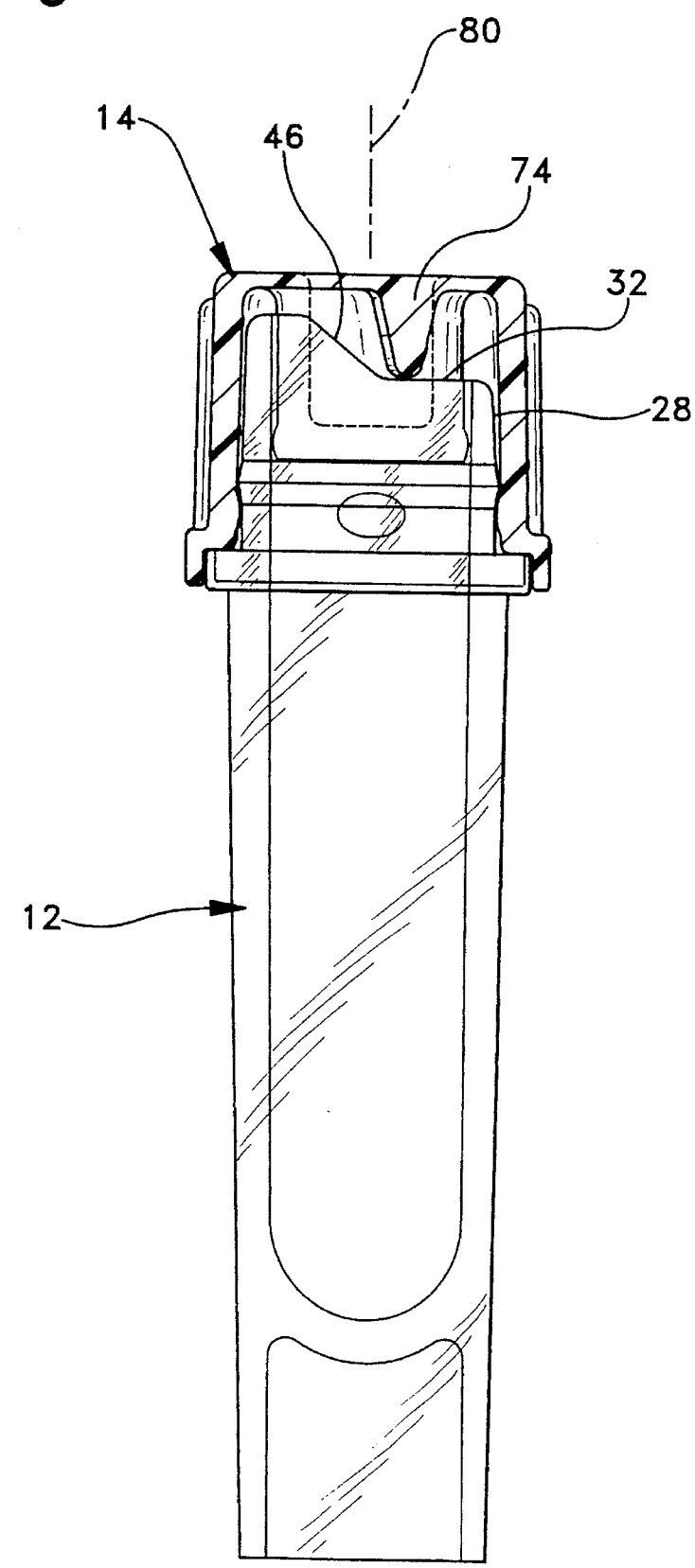
FIG. 6 is another side elevational view of the container of FIG. 1 with the cap secured but rotated so that the cam follower is at the base of the cam surface of the lip portion.
Figure 7:
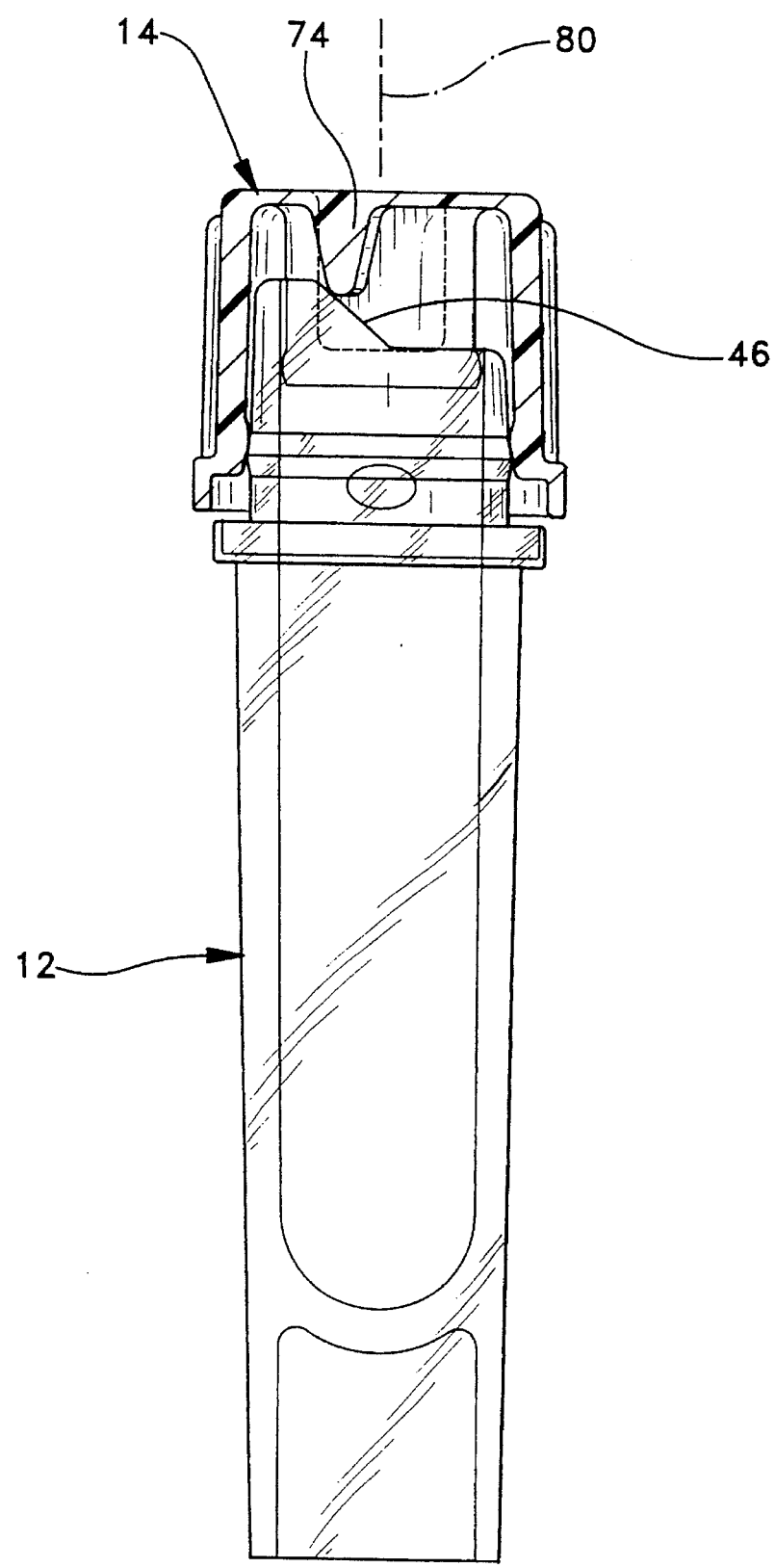
FIG. 7 is another side elevational view of the container of FIG. 1 with the cap unsecured and the cam follower near the top of the cam surface of the lip portion.

Cap 14 is unsecured from the container in a twist-off manner by applying a rotational force about longitudinal axis 80 while holding container 12. Rotation of cap 14 with respect to container 12 causes cam follower surface 74 to follow top surface 32 on upper portion 28 to the base of one of two cam surfaces 46, as shown in FIG. 6. As the cap 14 is rotated further, cam follower surface 74 rises on one of the cam surfaces 46 and in turn cap 14 is unsecured from container 12, as shown in FIG. 7. The rotational force applied to cap 14 can be bi-directional, that is clockwise or counter-clockwise.

The collection assembly of the invention may be made of a molded thermoplastic material so that the specimen collected may be readily viewed. Representative materials include, for example, polyethylene, polypropylene and polyvinyl chloride. The collection container may incorporate a hydrophilic material or a silicon, or a texture may be applied to the internal surface thereof for enhancing the flow and mixing of blood introduced into the container.

Although it is within the purview of the invention to provide caps which are colored to define specific forms of fluid collection containers containing materials for one reason or another or for defining the kind of examination to be conducted on the specimen collected, transparent caps may be provided. Also, it should be noted that the dimensions of the container are such as to provide space for labeling which may be important for identifying the collected specimens.

What is claimed is:

1. A collection assembly comprising a cap comprising a top and a bottom, an outer skirt extending from said top to said bottom and having an inner surface, an inverted recessed skirt surrounded by said outer skirt and extending from said top toward said bottom with a space between said inverted recessed skirt and said outer skirt, and a cam follower integral with said outer skirt and said inverted recessed skirt and extending from said top into said space; and a container comprising an open top, a closed bottom, and an integral lip extending from said open top and having an inner surface and a top surface, said top surface of said integral lip having a receiving edge that forms a cam surface having a shape that interacts with said cam follower in said cap to facilitate removal of said cap from said container upon rotation of said cap.

2. The assembly of claim 1, wherein said container further comprises:

a side wall having an outer surface;

a cap seating flange on said outer surface of said container positioned where said integral lip extends from said open top; and a locking ring on said outer surface of said container positioned between said integral lip and said cap seating flange.

3. The assembly of claim 2, wherein said cap further comprises:

at least one protrusion positioned on said inner surface of said outer skirt of said cap;

a sealing ring on said inverted recessed skirt of said cap; and a shield extending from said outer skirt of said cap;

wherein said protrusion bears against said locking ring of said container, said sealing ring bears against said inner surface of said integral lip of said container and said shield abuts with said cap seating flange when said cap is locked on said open top of said container.

4. The assembly of claim 2, wherein said container further comprises an annular skirt extending from said closed bottom and said outer surface of said sidewall.

5. The assembly of claim 2, further comprising a trough within said cap seating flange.

6. The assembly of claim 1, wherein said cap further comprises a shield extending from said outer skirt of said cap, said shield having a flat portion to prevent rolling of said cap and to provide a grasping surface for ready removal of said cap from said container.

7. The assembly of claim 1, wherein:

said integral lip includes a receiving edge for receiving a sample during sample collection and a pair of cam surfaces connecting said receiving edge to a lower portion of said integral lip; and said cam follower within said cap interacts with one of said cam surfaces to provide means for removing said cap from said container when said cap is rotated on said container.

8. The assembly of claim 1, wherein said cam follower interacts with said integral lip to remove said cap from said container when said cap is rotated in either a clockwise direction or a counter-clockwise direction with respect to a longitudinal axis of said container.

9. The assembly of claim 1, wherein said cam follower has a triangular shape.

10. A collection assembly comprising:

a container comprising an open top, a closed bottom, a sidewall extending from said top open to said closed bottom and having an inner surface and an outer surface, an integral lip extending from said open top to a receiving edge that forms a cam surface, a cap seating flange extending from said outer surface of said sidewall, a trough contained in the said cap seating flange, and a locking ring located between said integral lip and said cap seating flange; and a cap comprising a top and a bottom for abutting with said cap seating flange when said cap is locked on said open top of said container, an outer skirt extending from said top to said bottom and having an inner surface, an inverted recessed skirt surrounded by said outer skirt with a space between said outer skirt and said inverted recessed skirt for receiving said integral lip when said cap is placed over said open top of said container, and a cam follower integral with said outer skirt and said inverted recessed skirt and extending from said top into said space that contacts said cam surface on said integral lip of said container when said cap is placed over said open top of said container, said cam follower within said cap interacting with said cam surface of said integral lip of said container to remove said cap from said container when said cap is rotated on said container.

* * * * *